US008048119B2

(12) United States Patent
Bruneau et al.

(10) Patent No.: US 8,048,119 B2
(45) Date of Patent: Nov. 1, 2011

(54) APPARATUS FOR INSERTION BETWEEN ANATOMICAL STRUCTURES AND A PROCEDURE UTILIZING SAME

(75) Inventors: Aurelien Bruneau, Memphis, TN (US); Eric C. Lange, Collierville, TN (US); Kent M. Anderson, Memphis, TN (US); Randall Allard, Germantown, TN (US)

(73) Assignee: Warsaw Orthopedic, Inc., Warsaw, IN (US)

( * ) Notice: Subject to any disclaimer, the term of this patent is extended or adjusted under 35 U.S.C. 154(b) by 790 days.

(21) Appl. No.: 11/490,010

(22) Filed: Jul. 20, 2006

(65) Prior Publication Data

US 2008/0021460 A1   Jan. 24, 2008

(51) Int. Cl.
*A61B 17/70* (2006.01)

(52) U.S. Cl. .................................. 606/249; 623/17.12

(58) Field of Classification Search .......... 606/246–249, 606/86 A; 623/17.11–16; 29/451, 525.01
See application file for complete search history.

(56) References Cited

U.S. PATENT DOCUMENTS

| 624,969 | A | 5/1899 | Peterson |
| 1,153,797 | A | 9/1915 | Kegreisz |
| 1,516,347 | A | 11/1924 | Pataky |
| 1,870,942 | A | 8/1932 | Beatty |
| 2,077,804 | A | 4/1937 | Morrison |
| 2,299,308 | A | 10/1942 | Creighton |
| 2,485,531 | A | 10/1949 | Dzus et al. |
| 2,607,370 | A | 8/1952 | Anderson |
| 2,677,369 | A | 5/1954 | Knowles |
| 2,685,877 | A | 8/1954 | Dobelle |
| 3,065,659 | A | 11/1962 | Eriksson et al. |
| 3,108,595 | A | 10/1963 | Overment |
| 3,397,699 | A | 8/1968 | Kohl |
| 3,426,364 | A | 2/1969 | Lumb |
| 3,648,691 | A | 3/1972 | Lumb et al. |
| 3,779,239 | A | 12/1973 | Fischer et al. |
| 3,867,728 | A | 2/1975 | Stubstad et al. |
| 4,011,602 | A | 3/1977 | Rybicki et al. |
| 4,237,875 | A | 12/1980 | Termanini |
| 4,257,409 | A | 3/1981 | Bacal et al. |
| 4,274,324 | A | 6/1981 | Giannuzzi |
| 4,289,123 | A | 9/1981 | Dunn |
| 4,327,736 | A | 5/1982 | Inoue |
| 4,401,112 | A | 8/1983 | Rezaian |

(Continued)

FOREIGN PATENT DOCUMENTS

DE   2821678 A1   11/1979

(Continued)

OTHER PUBLICATIONS

European Patent Office, International Searching Authority, Notification of Transmittal of the International Search Report and the Written Opinion of the International Searching Authority or the Declaration, International Application No. PCT/US2007/066051, Sep. 6, 2007, 12 pages.

(Continued)

*Primary Examiner* — Eduardo C Robert
*Assistant Examiner* — Steven J Cotroneo

(57) ABSTRACT

A surgical procedure and apparatus according to which force is applied to a member to compress the member, and the member is retained in its compressed state while it is inserted between two anatomical structures. The member is then allowed to move from its compressed state towards its original state and into engagement with the structures.

5 Claims, 6 Drawing Sheets

U.S. PATENT DOCUMENTS

| | | |
|---|---|---|
| 4,499,636 A | 2/1985 | Tanaka |
| 4,519,100 A | 5/1985 | Wills et al. |
| 4,553,273 A | 11/1985 | Wu |
| 4,554,914 A | 11/1985 | Kapp et al. |
| 4,573,454 A | 3/1986 | Hoffman |
| 4,592,341 A | 6/1986 | Omagari et al. |
| 4,599,086 A | 7/1986 | Doty |
| 4,604,995 A | 8/1986 | Stephens et al. |
| 4,611,582 A | 9/1986 | Duff |
| 4,632,101 A | 12/1986 | Freedland |
| 4,636,217 A | 1/1987 | Ogilvie et al. |
| 4,646,998 A | 3/1987 | Pate |
| 4,657,550 A | 4/1987 | Daher |
| 4,662,808 A | 5/1987 | Camilleri |
| 4,686,970 A | 8/1987 | Dove et al. |
| 4,704,057 A | 11/1987 | McSherry |
| 4,721,103 A | 1/1988 | Freedland |
| 4,759,769 A | 7/1988 | Hedman et al. |
| 4,787,378 A | 11/1988 | Sodhi |
| 4,822,226 A | 4/1989 | Kennedy |
| 4,827,918 A | 5/1989 | Olerud |
| 4,834,600 A | 5/1989 | Lemke |
| 4,863,476 A | 9/1989 | Shepperd |
| 4,886,405 A | 12/1989 | Blomberg |
| 4,892,545 A | 1/1990 | Day et al. |
| 4,913,144 A | 4/1990 | Del Medico |
| 4,931,055 A | 6/1990 | Bumpus et al. |
| 4,932,975 A | 6/1990 | Main et al. |
| 4,969,887 A | 11/1990 | Sodhi |
| 4,969,888 A | 11/1990 | Scholten et al. |
| 5,000,166 A | 3/1991 | Karpf |
| 5,011,484 A | 4/1991 | Breard |
| 5,047,055 A | 9/1991 | Bao et al. |
| 5,059,193 A | 10/1991 | Kuslich |
| 5,092,866 A | 3/1992 | Breard et al. |
| 5,098,433 A | 3/1992 | Freedland |
| 5,171,278 A | 12/1992 | Pisharodi |
| 5,171,280 A | 12/1992 | Baumgartner |
| 5,201,734 A | 4/1993 | Cozad et al. |
| 5,267,999 A | 12/1993 | Olerud |
| 5,290,312 A | 3/1994 | Kojimoto et al. |
| 5,306,275 A | 4/1994 | Bryan |
| 5,306,310 A | 4/1994 | Siebels |
| 5,312,405 A | 5/1994 | Korotko et al. |
| 5,316,422 A | 5/1994 | Coffman |
| 5,356,423 A | 10/1994 | Tihon et al. |
| 5,360,430 A | 11/1994 | Lin |
| 5,366,455 A | 11/1994 | Dove |
| 5,370,697 A | 12/1994 | Baumgartner |
| 5,390,683 A | 2/1995 | Pisharodi |
| 5,395,370 A | 3/1995 | Muller et al. |
| 5,401,269 A | 3/1995 | Buttner-Janz et al. |
| 5,403,316 A | 4/1995 | Ashman |
| 5,415,661 A | 5/1995 | Holmes |
| 5,437,672 A | 8/1995 | Alleyne |
| 5,437,674 A | 8/1995 | Worcel et al. |
| 5,439,463 A | 8/1995 | Lin |
| 5,454,812 A | 10/1995 | Lin |
| 5,456,689 A | 10/1995 | Kresch et al. |
| 5,458,641 A | 10/1995 | Ramirez Jimenez |
| 5,480,442 A | 1/1996 | Bertagnoli |
| 5,496,318 A | 3/1996 | Howland et al. |
| 5,518,498 A | 5/1996 | Lindenberg et al. |
| 5,549,679 A | 8/1996 | Kuslich |
| 5,554,191 A | 9/1996 | Lahille et al. |
| 5,562,662 A | 10/1996 | Brumfield et al. |
| 5,562,735 A | 10/1996 | Margulies |
| 5,562,736 A | 10/1996 | Ray et al. |
| 5,571,192 A | 11/1996 | Schonhoffer |
| 5,609,634 A | 3/1997 | Voydeville |
| 5,609,635 A | 3/1997 | Michelson |
| 5,628,756 A | 5/1997 | Barker, Jr. et al. |
| 5,630,816 A | 5/1997 | Kambin |
| 5,645,597 A | 7/1997 | Krapiva |
| 5,645,599 A | 7/1997 | Samani |
| 5,653,762 A | 8/1997 | Pisharodi |
| 5,653,763 A | 8/1997 | Errico et al. |
| 5,658,335 A | 8/1997 | Allen |
| 5,665,122 A | 9/1997 | Kambin |
| 5,674,295 A | 10/1997 | Ray et al. |
| 5,676,702 A | 10/1997 | Ratron |
| 5,685,826 A | 11/1997 | Bonutti |
| 5,690,649 A | 11/1997 | Li |
| 5,693,100 A | 12/1997 | Pisharodi |
| 5,702,395 A | 12/1997 | Hopf |
| 5,702,452 A | 12/1997 | Argenson et al. |
| 5,702,454 A | 12/1997 | Baumgartner |
| 5,702,455 A | 12/1997 | Saggar |
| 5,707,390 A | 1/1998 | Bonutti |
| 5,716,416 A | 2/1998 | Lin |
| 5,723,013 A | 3/1998 | Jeanson et al. |
| 5,725,341 A | 3/1998 | Hofmeister |
| 5,746,762 A | 5/1998 | Bass |
| 5,755,797 A | 5/1998 | Baumgartner |
| 5,800,547 A | 9/1998 | Schafer et al. |
| 5,800,549 A | 9/1998 | Bao et al. |
| 5,810,815 A | 9/1998 | Morales |
| 5,836,948 A | 11/1998 | Zucherman et al. |
| 5,849,004 A | 12/1998 | Bramlet |
| 5,860,977 A | 1/1999 | Zucherman et al. |
| 5,888,196 A | 3/1999 | Bonutti |
| 5,941,881 A | 8/1999 | Barnes |
| 5,964,730 A * | 10/1999 | Williams et al. ............... 604/103 |
| 5,976,186 A | 11/1999 | Bao et al. |
| 5,980,523 A | 11/1999 | Jackson |
| 6,022,376 A | 2/2000 | Assell et al. |
| 6,048,342 A | 4/2000 | Zucherman et al. |
| 6,059,829 A | 5/2000 | Schlapher et al. |
| 6,066,154 A | 5/2000 | Reiley et al. |
| 6,068,630 A | 5/2000 | Zucherman et al. |
| 6,074,390 A | 6/2000 | Zucherman et al. |
| 6,113,638 A | 9/2000 | Williams et al. |
| 6,126,689 A | 10/2000 | Brett |
| 6,126,691 A | 10/2000 | Kasra et al. |
| 6,127,597 A | 10/2000 | Beyar et al. |
| 6,132,464 A | 10/2000 | Martin |
| 6,143,031 A | 11/2000 | Knothe et al. |
| 6,190,413 B1 | 2/2001 | Sutcliffe |
| 6,190,414 B1 | 2/2001 | Young |
| 6,214,037 B1 | 4/2001 | Mitchell et al. |
| 6,214,050 B1 | 4/2001 | Huene |
| 6,224,631 B1 | 5/2001 | Kohrs |
| 6,245,107 B1 | 6/2001 | Ferree |
| 6,293,949 B1 | 9/2001 | Justis et al. |
| 6,325,827 B1 | 12/2001 | Lin |
| 6,336,930 B1 | 1/2002 | Stalcup et al. |
| 6,348,053 B1 | 2/2002 | Cachia |
| 6,352,537 B1 | 3/2002 | Strnad |
| 6,364,883 B1 | 4/2002 | Santilli |
| 6,371,987 B1 | 4/2002 | Weiland et al. |
| 6,375,682 B1 | 4/2002 | Fleischmann et al. |
| 6,383,221 B1 | 5/2002 | Scarborough et al. |
| 6,402,750 B1 | 6/2002 | Atkinson et al. |
| 6,402,751 B1 | 6/2002 | Hoeck et al. |
| 6,419,703 B1 | 7/2002 | Fallin et al. |
| 6,419,704 B1 | 7/2002 | Ferree |
| 6,432,130 B1 | 8/2002 | Hanson |
| 6,440,169 B1 | 8/2002 | Elberg et al. |
| 6,447,513 B1 | 9/2002 | Griggs |
| 6,451,019 B1 | 9/2002 | Zucherman et al. |
| 6,500,178 B2 | 12/2002 | Zucherman et al. |
| 6,511,508 B1 | 1/2003 | Shahinpoor et al. |
| 6,514,256 B2 | 2/2003 | Zucherman et al. |
| 6,520,991 B2 | 2/2003 | Huene |
| 6,554,833 B2 | 4/2003 | Levy |
| 6,582,433 B2 | 6/2003 | Yun |
| 6,582,467 B1 | 6/2003 | Teitelbaum et al. |
| 6,592,585 B2 | 7/2003 | Lee et al. |
| 6,626,944 B1 | 9/2003 | Taylor |
| 6,645,207 B2 | 11/2003 | Dixon et al. |
| 6,669,729 B2 | 12/2003 | Chin |
| 6,685,742 B1 | 2/2004 | Jackson |
| 6,695,842 B2 | 2/2004 | Zucherman et al. |
| 6,699,246 B2 | 3/2004 | Zucherman et al. |
| 6,709,435 B2 | 3/2004 | Lin |
| 6,723,126 B1 | 4/2004 | Berry |
| 6,730,126 B2 | 5/2004 | Boehm, Jr. et al. |

| Patent/Publication | Date | Name |
|---|---|---|
| 6,733,533 B1 | 5/2004 | Lozier |
| 6,733,534 B2 | 5/2004 | Sherman |
| 6,736,818 B2 | 5/2004 | Perren et al. |
| 6,743,257 B2 | 6/2004 | Castro |
| 6,758,863 B2 | 7/2004 | Estes et al. |
| 6,761,720 B1 | 7/2004 | Senegas |
| 6,770,096 B2 | 8/2004 | Bolger et al. |
| 6,783,530 B1 | 8/2004 | Levy |
| 6,835,205 B2 | 12/2004 | Atkinson et al. |
| 6,902,580 B2 | 6/2005 | Fallin et al. |
| 6,905,512 B2 | 6/2005 | Paes et al. |
| 6,936,070 B1 | 8/2005 | Muhanna |
| 6,946,000 B2 | 9/2005 | Senegas et al. |
| 6,958,077 B2 | 10/2005 | Suddaby |
| 6,969,404 B2 | 11/2005 | Ferree |
| 6,981,975 B2 | 1/2006 | Michelson |
| 6,981,981 B2 | 1/2006 | Reiley et al. |
| 7,011,685 B2 | 3/2006 | Arnin et al. |
| 7,041,136 B2 | 5/2006 | Goble et al. |
| 7,048,736 B2 | 5/2006 | Robinson et al. |
| 7,070,598 B2 | 7/2006 | Lim et al. |
| 7,081,120 B2 | 7/2006 | Li et al. |
| 7,087,055 B2 | 8/2006 | Lim et al. |
| 7,087,083 B2 | 8/2006 | Pasquet et al. |
| 7,097,648 B1 | 8/2006 | Globerman et al. |
| 7,097,654 B1 | 8/2006 | Freedland |
| 7,101,375 B2 | 9/2006 | Zucherman et al. |
| 7,163,558 B2 | 1/2007 | Senegas et al. |
| 7,201,751 B2 | 4/2007 | Zucherman et al. |
| 7,201,772 B2 | 4/2007 | Schwammenthal et al. |
| 7,217,293 B2 | 5/2007 | Branch, Jr. |
| 7,238,204 B2 | 7/2007 | Le Couedic et al. |
| 7,306,628 B2 | 12/2007 | Zucherman et al. |
| 7,335,203 B2 | 2/2008 | Winslow et al. |
| 7,377,942 B2 | 5/2008 | Berry |
| 7,431,735 B2 | 10/2008 | Liu et al. |
| 7,442,208 B2 | 10/2008 | Mathieu et al. |
| 7,445,637 B2 | 11/2008 | Taylor |
| 7,458,981 B2 | 12/2008 | Fielding et al. |
| 7,582,106 B2 | 9/2009 | Teitelbaum et al. |
| 7,604,652 B2 | 10/2009 | Arnin et al. |
| 7,611,316 B2 | 11/2009 | Panasik et al. |
| 7,621,950 B1 | 11/2009 | Globerman et al. |
| 7,658,752 B2 | 2/2010 | Labrom et al. |
| 7,749,252 B2 | 7/2010 | Zucherman et al. |
| 7,771,456 B2 | 8/2010 | Hartmann et al. |
| 7,901,430 B2 | 3/2011 | Matsuura et al. |
| 2001/0016743 A1 | 8/2001 | Zucherman et al. |
| 2001/0049531 A1 | 12/2001 | Reiley et al. |
| 2002/0082600 A1 | 6/2002 | Shaolian et al. |
| 2002/0143331 A1 | 10/2002 | Zucherman et al. |
| 2003/0040746 A1 | 2/2003 | Mitchell et al. |
| 2003/0045940 A1 | 3/2003 | Eberlein et al. |
| 2003/0065330 A1 | 4/2003 | Zucherman et al. |
| 2003/0144737 A1* | 7/2003 | Sherman ............ 623/17.12 |
| 2003/0153915 A1 | 8/2003 | Nekozuka et al. |
| 2003/0195628 A1 | 10/2003 | Bao et al. |
| 2003/0220649 A1 | 11/2003 | Bao et al. |
| 2004/0010312 A1 | 1/2004 | Enayati |
| 2004/0010316 A1 | 1/2004 | William et al. |
| 2004/0083002 A1 | 4/2004 | Belef et al. |
| 2004/0087947 A1 | 5/2004 | Lim et al. |
| 2004/0097931 A1 | 5/2004 | Mitchell |
| 2004/0106995 A1 | 6/2004 | Le Couedic et al. |
| 2004/0117017 A1 | 6/2004 | Pasquet et al. |
| 2004/0133204 A1 | 7/2004 | Davies |
| 2004/0133280 A1 | 7/2004 | Trieu |
| 2004/0167625 A1 | 8/2004 | Beyar et al. |
| 2004/0186576 A1 | 9/2004 | Biscup et al. |
| 2004/0199255 A1 | 10/2004 | Mathieu et al. |
| 2004/0215070 A1* | 10/2004 | Letort et al. ............ 600/364 |
| 2004/0243239 A1* | 12/2004 | Taylor ............ 623/17.13 |
| 2004/0260397 A1 | 12/2004 | Lambrecht et al. |
| 2005/0010293 A1 | 1/2005 | Zucherman et al. |
| 2005/0015140 A1 | 1/2005 | deBeer |
| 2005/0027358 A1 | 2/2005 | Suddaby |
| 2005/0033434 A1 | 2/2005 | Berry |
| 2005/0049708 A1 | 3/2005 | Atkinson et al. |
| 2005/0055031 A1 | 3/2005 | Lim |
| 2005/0085814 A1 | 4/2005 | Sherman et al. |
| 2005/0143827 A1 | 6/2005 | Globerman et al. |
| 2005/0165398 A1 | 7/2005 | Reiley |
| 2005/0203512 A1 | 9/2005 | Hawkins et al. |
| 2005/0203519 A1 | 9/2005 | Harms et al. |
| 2005/0203624 A1 | 9/2005 | Serhan et al. |
| 2005/0228391 A1 | 10/2005 | Levy et al. |
| 2005/0245937 A1 | 11/2005 | Winslow |
| 2005/0261768 A1* | 11/2005 | Trieu ............ 623/17.11 |
| 2005/0261781 A1* | 11/2005 | Sennett et al. ............ 623/23.54 |
| 2005/0267579 A1 | 12/2005 | Reiley et al. |
| 2005/0273166 A1 | 12/2005 | Sweeney |
| 2005/0288672 A1 | 12/2005 | Ferree |
| 2006/0004447 A1 | 1/2006 | Mastrorio et al. |
| 2006/0004455 A1 | 1/2006 | Leonard et al. |
| 2006/0015181 A1 | 1/2006 | Elberg |
| 2006/0064165 A1 | 3/2006 | Zucherman et al. |
| 2006/0084983 A1* | 4/2006 | Kim ............ 606/61 |
| 2006/0084985 A1 | 4/2006 | Kim |
| 2006/0084987 A1 | 4/2006 | Kim |
| 2006/0084988 A1 | 4/2006 | Kim |
| 2006/0085069 A1 | 4/2006 | Kim |
| 2006/0085070 A1 | 4/2006 | Kim |
| 2006/0085074 A1 | 4/2006 | Raiszadeh |
| 2006/0089654 A1 | 4/2006 | Lins et al. |
| 2006/0089719 A1 | 4/2006 | Trieu |
| 2006/0095136 A1 | 5/2006 | McLuen |
| 2006/0106381 A1 | 5/2006 | Ferree et al. |
| 2006/0106397 A1 | 5/2006 | Lins |
| 2006/0111728 A1 | 5/2006 | Abdou |
| 2006/0116690 A1 | 6/2006 | Pagano |
| 2006/0122620 A1 | 6/2006 | Kim |
| 2006/0129239 A1 | 6/2006 | Kwak |
| 2006/0136060 A1 | 6/2006 | Taylor |
| 2006/0149242 A1 | 7/2006 | Kraus et al. |
| 2006/0182515 A1 | 8/2006 | Panasik et al. |
| 2006/0184247 A1 | 8/2006 | Edidin et al. |
| 2006/0184248 A1 | 8/2006 | Edidin et al. |
| 2006/0195102 A1 | 8/2006 | Malandain |
| 2006/0217726 A1 | 9/2006 | Maxy et al. |
| 2006/0224159 A1 | 10/2006 | Anderson |
| 2006/0224241 A1 | 10/2006 | Butler et al. |
| 2006/0235387 A1 | 10/2006 | Peterman |
| 2006/0235532 A1 | 10/2006 | Meunier et al. |
| 2006/0241601 A1 | 10/2006 | Trautwein et al. |
| 2006/0241613 A1 | 10/2006 | Bruneau et al. |
| 2006/0241643 A1 | 10/2006 | Lim et al. |
| 2006/0241757 A1 | 10/2006 | Anderson |
| 2006/0247623 A1 | 11/2006 | Anderson et al. |
| 2006/0247640 A1 | 11/2006 | Blackwell et al. |
| 2006/0264938 A1 | 11/2006 | Zucherman et al. |
| 2006/0271044 A1 | 11/2006 | Petrini et al. |
| 2006/0271049 A1 | 11/2006 | Zucherman et al. |
| 2006/0271061 A1 | 11/2006 | Beyar et al. |
| 2006/0282075 A1 | 12/2006 | Labrom et al. |
| 2006/0282079 A1 | 12/2006 | Labrom et al. |
| 2006/0293662 A1 | 12/2006 | Boyer, II et al. |
| 2006/0293663 A1 | 12/2006 | Walkenhorst et al. |
| 2007/0005064 A1 | 1/2007 | Anderson et al. |
| 2007/0010813 A1 | 1/2007 | Zucherman et al. |
| 2007/0032790 A1 | 2/2007 | Aschmann et al. |
| 2007/0043362 A1 | 2/2007 | Malandain et al. |
| 2007/0043363 A1 | 2/2007 | Malandain et al. |
| 2007/0049935 A1 | 3/2007 | Edidin et al. |
| 2007/0055274 A1 | 3/2007 | Appenzeller et al. |
| 2007/0073289 A1 | 3/2007 | Kwak et al. |
| 2007/0100340 A1 | 5/2007 | Lange et al. |
| 2007/0123861 A1 | 5/2007 | Dewey et al. |
| 2007/0142915 A1 | 6/2007 | Altarac et al. |
| 2007/0151116 A1 | 7/2007 | Malandain |
| 2007/0162000 A1 | 7/2007 | Perkins |
| 2007/0162136 A1 | 7/2007 | O'Neil et al. |
| 2007/0167945 A1 | 7/2007 | Lange et al. |
| 2007/0173822 A1 | 7/2007 | Bruneau et al. |
| 2007/0173823 A1 | 7/2007 | Dewey et al. |
| 2007/0191833 A1 | 8/2007 | Bruneau et al. |
| 2007/0191834 A1 | 8/2007 | Bruneau et al. |
| 2007/0191837 A1 | 8/2007 | Trieu |
| 2007/0191838 A1 | 8/2007 | Bruneau et al. |

| | | | |
|---|---|---|---|
| 2007/0198091 A1 | 8/2007 | Boyer et al. | |
| 2007/0225807 A1 | 9/2007 | Phan et al. | |
| 2007/0233068 A1 | 10/2007 | Bruneau et al. | |
| 2007/0233074 A1 | 10/2007 | Anderson et al. | |
| 2007/0233076 A1* | 10/2007 | Trieu | 606/61 |
| 2007/0233081 A1 | 10/2007 | Pasquet et al. | |
| 2007/0233089 A1 | 10/2007 | DiPoto et al. | |
| 2007/0250060 A1* | 10/2007 | Anderson et al. | 606/61 |
| 2007/0270823 A1 | 11/2007 | Trieu et al. | |
| 2007/0270824 A1 | 11/2007 | Lim et al. | |
| 2007/0270825 A1 | 11/2007 | Carls et al. | |
| 2007/0270826 A1 | 11/2007 | Trieu et al. | |
| 2007/0270827 A1 | 11/2007 | Lim et al. | |
| 2007/0270828 A1 | 11/2007 | Bruneau et al. | |
| 2007/0270829 A1 | 11/2007 | Carls et al. | |
| 2007/0270834 A1 | 11/2007 | Bruneau et al. | |
| 2007/0270874 A1 | 11/2007 | Anderson | |
| 2007/0272259 A1 | 11/2007 | Allard et al. | |
| 2007/0276368 A1 | 11/2007 | Trieu et al. | |
| 2007/0276369 A1 | 11/2007 | Allard et al. | |
| 2007/0276493 A1 | 11/2007 | Malandain et al. | |
| 2007/0276496 A1 | 11/2007 | Lange et al. | |
| 2007/0276497 A1 | 11/2007 | Anderson | |
| 2007/0282443 A1 | 12/2007 | Globerman et al. | |
| 2008/0021457 A1 | 1/2008 | Anderson et al. | |
| 2008/0021460 A1 | 1/2008 | Bruneau et al. | |
| 2008/0058934 A1 | 3/2008 | Malandain et al. | |
| 2008/0097446 A1 | 4/2008 | Reiley et al. | |
| 2008/0114357 A1 | 5/2008 | Allard et al. | |
| 2008/0114358 A1 | 5/2008 | Anderson et al. | |
| 2008/0114456 A1 | 5/2008 | Dewey et al. | |
| 2008/0147190 A1 | 6/2008 | Dewey et al. | |
| 2008/0161818 A1 | 7/2008 | Kloss et al. | |
| 2008/0167685 A1 | 7/2008 | Allard et al. | |
| 2008/0183209 A1 | 7/2008 | Robinson et al. | |
| 2008/0183211 A1 | 7/2008 | Lamborne et al. | |
| 2008/0183218 A1 | 7/2008 | Mueller et al. | |
| 2008/0195152 A1 | 8/2008 | Altarac et al. | |
| 2008/0215094 A1 | 9/2008 | Taylor | |
| 2008/0221685 A9 | 9/2008 | Altarac et al. | |
| 2008/0234824 A1 | 9/2008 | Youssef et al. | |
| 2008/0262617 A1 | 10/2008 | Froehlich et al. | |
| 2008/0281360 A1 | 11/2008 | Vittur et al. | |
| 2008/0281361 A1 | 11/2008 | Vittur et al. | |
| 2009/0062915 A1 | 3/2009 | Kohm et al. | |
| 2009/0105766 A1 | 4/2009 | Thompson et al. | |
| 2009/0105773 A1 | 4/2009 | Lange et al. | |
| 2009/0234389 A1 | 9/2009 | Chuang et al. | |
| 2009/0240283 A1 | 9/2009 | Carls et al. | |
| 2009/0270918 A1 | 10/2009 | Attia et al. | |
| 2010/0121379 A1 | 5/2010 | Edmond | |
| 2010/0204732 A1 | 8/2010 | Aschmann et al. | |

FOREIGN PATENT DOCUMENTS

| | | |
|---|---|---|
| DE | 3922044 A1 | 2/1991 |
| DE | 4012622 C1 | 7/1991 |
| EP | 0322334 B1 | 2/1992 |
| EP | 0767636 B1 | 1/1999 |
| EP | 1004276 A1 | 5/2000 |
| EP | 1011464 B1 | 6/2000 |
| EP | 1138268 A1 | 10/2001 |
| EP | 1148850 B1 | 10/2001 |
| EP | 1148851 B1 | 10/2001 |
| EP | 1302169 A1 | 4/2003 |
| EP | 1330987 A1 | 7/2003 |
| EP | 1552797 A2 | 7/2005 |
| EP | 1854433 A1 | 11/2007 |
| EP | 1905392 A1 | 4/2008 |
| EP | 1982664 A1 | 10/2008 |
| FR | 2623085 A1 | 5/1989 |
| FR | 2625097 A1 | 6/1989 |
| FR | 2681525 A1 | 3/1993 |
| FR | 2700941 A1 | 8/1994 |
| FR | 2703239 A1 | 10/1994 |
| FR | 2707864 A1 | 1/1995 |
| FR | 2717675 A1 | 9/1995 |
| FR | 2722087 A1 | 1/1996 |
| FR | 2722088 A1 | 1/1996 |
| FR | 2724554 A1 | 3/1996 |
| FR | 2725892 A1 | 4/1996 |
| FR | 2730156 A1 | 8/1996 |
| FR | 2731643 A1 | 9/1996 |
| FR | 2775183 A1 | 8/1999 |
| FR | 2799948 A1 | 4/2001 |
| FR | 2816197 A1 * | 5/2002 |
| IL | 2005002466 A2 | 1/2005 |
| JP | 02-224660 | 9/1990 |
| JP | 09-075381 | 3/1997 |
| JP | 2003-079649 | 3/2003 |
| SU | 988281 | 1/1983 |
| SU | 1484348 A1 | 6/1989 |
| SU | 1484348 | 7/1989 |
| WO | WO 94/26192 | 11/1994 |
| WO | WO 94/26195 | 11/1994 |
| WO | WO 97/18769 | 5/1997 |
| WO | WO 98/20939 | 5/1998 |
| WO | WO 99/26562 | 6/1999 |
| WO | WO 99/59669 | 11/1999 |
| WO | WO 00/44319 | 8/2000 |
| WO | WO 01/54598 A1 | 8/2001 |
| WO | 2006025815 A1 | 3/2002 |
| WO | WO 03/057055 A1 | 7/2003 |
| WO | 2004/084743 A1 | 4/2004 |
| WO | WO 2004/047689 A1 | 6/2004 |
| WO | WO 2004/047691 A1 | 6/2004 |
| WO | WO 2004/084768 A2 | 10/2004 |
| WO | 2004/110300 A2 | 12/2004 |
| WO | WO 2005/002474 A1 | 1/2005 |
| WO | 2005/009300 | 2/2005 |
| WO | WO 2005/009300 | 2/2005 |
| WO | WO 2005/011507 A1 | 2/2005 |
| WO | WO 2005/044118 A1 | 5/2005 |
| WO | WO 2005/048856 A1 | 6/2005 |
| WO | WO 2005/110258 A1 | 11/2005 |
| WO | WO 2006/064356 A1 | 6/2006 |
| WO | WO 2007/034516 A1 | 3/2007 |
| WO | 2007038349 A2 | 4/2007 |
| WO | WO2007052975 A | 5/2007 |
| WO | WO 2007052975 A | 5/2007 |
| WO | WO 2009/083276 A1 | 7/2009 |
| WO | WO 2009/083583 A1 | 7/2009 |
| WO | WO 2009/098536 A1 | 8/2009 |

OTHER PUBLICATIONS

European Patent Office, International Searching Authority,Notification of Transmittal of the International Search Report and the Written Opinion of the International Searching Authority or the Declaration, International Application No. PCT/US2007/073604, Dec. 17, 2007, 13 pages.
U.S. Appl. No. 11/438,763, filed May 23, 2006, Allard, et al.
U.S. Appl. No. 11/417,382, filed May 4, 2006, Bruneau, et al.
U.S. Appl. No. 11/409,639, filed Apr. 24, 2006, Anderson.
U.S. Appl. No. 11/409,641, filed Apr. 24, 2006, Anderson, et al.
U.S. Appl. No. 11/376,991, filed Mar. 16, 2006, Anderson, et al.
U.S. Appl. No. 11/359,070, filed Feb. 22, 2006, Bruneau. et al.
U.S. Appl. No. 11/333,919, filed Jan. 18, 2006, Dewey, et al.
U.S. Appl. No. 11/334,691, filed Jan. 18, 2006, Lange, et al.
U.S. Appl. No. 11/271,018, filed Nov. 10, 2005, Dewey, et al.
U.S. Appl. No. 11/261,386, filed Oct. 27, 2005, Lange, et al.
U.S. Appl. No. 11/167,775, filed Jun. 27, 2005, Anderson, et al.
U.S. Appl. No. 11/095,215, filed Mar. 31, 2005, Anderson.
U.S. Appl. No. 11/095,214, filed Mar. 31, 2005, Anderson.
European Patent Office, International Searching Authority, Notification of Transmittal of the International Search Report and the Written Opinion of the International Searching Authority or the Declaration, International Application No. PCT/US2007/062405, Aug. 2, 2007, 9 pages.
"Dispositivo Intervertebrale Ammortizzante DIAM," date unknown, p. 1.
"Tecnica Operatoria Per II Posizionamento Della Protesi DIAM," date unknown, pp. 1-3.
"Wallis Operative Technique: Surgical Procedure for Treatment of Degenerative Disc Disease (DDD) of Lumbar Spine," date unknown, pp. 1-24, Spine Next, an Abbott Laboratories company, Bordeaux, France.

Benzel et al., "Posterior Cervical Interspinous Compression Wiring and Fusion for Mid to Low Cervical Spinal Injuries," J. Neurosurg., Jun. 1989, pp. 893-899, vol. 70.

Caserta et al., "Elastic Stabilization Alone or Combined with Rigid Fusion in Spinal Surgery: a Biomechanical Study and Clinical Experience Based on 82 Cases," Eur. Spine J., Oct. 2002, pp. S192-S197, vol. 11, Suppl. 2.

Christie et al., "Dynamic Interspinous Process Technology," SPINE, 2005, pp. S73-S78, vol. 30, No. 16S.

Cousin Biotech, "Analysis of Clinical Experience with a Posterior Shock-Absorbing Implant," date unknown, pp. 2-9.

Cousin Biotech, Dispositif Intervertébral Amortissant, Jun. 1998, pp. 1-4.

Cousin Biotech, Technique Operatoire de la Prothese DIAM, date unknown, Annexe 1, pp. 1-8.

Dickman et al., "The Interspinous Method of Posterior Atlantoaxial Arthrodesis," J. Neurosurg., Feb. 1991, pp. 190-198, vol. 74.

Dubois et al., "Dynamic Neutralization: A New Concept for Restabilization of the Spine," Lumbar Segmental Insability, Szpalski et al., eds., 1999, pp. 233-240, Lippincott Williams & Wilkins, Philadelphia, Pennsylvania.

Duff, "Methyl Methacrylate in Spinal Stabilization," Techniques in Spinal Fusion and Stabilization, Hitchon et al., eds., 1995, pp. 147-151, Ch. 14, Thieme, New York.

Ebara et al., "Inoperative Measurement of Lumbar Spinal Instability," SPINE, 1992, pp. S44-S50, vol. 17, No. 3S.

Fassio et al., "Treatment of Degenerative Lumbar Spinal Instability L4-L5 by Interspinous Ligamentoplasty," Rachis, Dec. 1991, pp. 465-474, vol. 3, No. 6.

Fassio, "Mise au Point Sur la Ligamentoplastie Inter-Epineuse Lombaire Dans les Instabilites," Maîtrise Orthopédique, Jul. 1993, pp. 18, No. 25.

Garner et al., "Development and Preclinical Testing of a New Tension-Band Device for the Spine: the Loop System," Eur. Spine J., Aug. 7, 2002, pp. S186-S191, vol. 11, Suppl. 2.

Guang et al., "Interspinous Process Segmental Instrumentation with Bone-Button-Wire for Correction of Scoliosis," Chinese Medical J., 1990, pp. 721-725, vol. 103.

Guizzardi et al., "The Use of DIAM (Interspinous Stress-Breaker Device) in the Prevention of Chronic-Low Back Pain in Young Patients Operated on for Large Dimension Lumbar Disc Herniation," 12th Eur. Cong. Neurosurg., Sep. 7-12, 2003, pp. 835-839, Port.

Hambly et al., "Tension Band Wiring-Bone Grafting for Spondylolysis and Spondylolisthesis," SPINE, 1989, pp. 455-460, vol. 14, No. 4.

Kiwerski, "Rehabilitation of Patients with Thoracic Spine Injury Treated by Spring Alloplasty," Int. J. Rehab. Research, 1983, pp. 469-474, vol. 6, No. 4.

Kramer et al., "Intevetertebral Disk Diseases: Causes, Diagnosis, Treatment and Prophylaxis," pp. 244-249, Medical, 1990.

Laudet et al., "Comportement Bio-Mécanique D'Un Ressort Inter-Apophysaire Vertébral Postérieur Analyse Expérimentale Due Comportement Discal En Compression Et En Flexion/Extension," Rachis, 1993, vol. 5, No. 2.

Mah et al., "Threaded K-Wire Spinous Process Fixation of the Axis for Modified Gallie Fusion in Children and Adolescents," J. Pediatric Othopaedics, 1989, pp. 675-679, vol. 9.

Mariottini et al., "Preliminary Results of a Soft Novel Lumbar Intervertebral Prothesis (DIAM) in the Degenerative Spinal Pathology," Acta Neurochir., Adv. Peripheral Nerve Surg. and Minimal Invas. Spinal Surg., 2005, pp. 129-131, vol. 92, Suppl.

McDonnell et al., "Posterior Atlantoaxial Fusion: Indications and Techniques," Techniques in Spinal Fusion and Stabilization, Hitchon et al., eds., 1995, pp. 92-106, Ch. 9, Thieme, New York.

Minns et al., "Preliminary Design and Experimental Studies of a Novel Soft Implant for Correcting Sagittal Plane Instability in the Lumbar Spine," SPINE, 1997, pp. 1819-1825, vol. 22, No. 16.

Müller, "Restauration Dynamique de la Stabilité Rachidienne," Tiré de la Sulzer Technical Review, Jan. 1999, Sulzer Management Ltd, Winterthur, Switzerland.

Pennal et al., "Stenosis of the Lumbar Spinal Canal," Clinical Neurosurgery: Proceedings of the Congress of Neurological Surgeons, St. Louis, Missouri, 1970, Tindall et al., eds., 1971, Ch. 6, pp. 86-105, vol. 18.

Petrini et al., "Analisi Di Un'Esperienza Clinica Con Un Impianto Posteriore Ammortizzante," S.O.T.I.M.I. Società di Ortopedia e Traumatologia dell'Italia Meridionale e Insulare 90° Congresso, Jun. 21-23, 2001, Paestum.

Petrini et al., "Stabilizzazione Elastica," Patologia Degenerativa del Rachide Lombare, Oct. 5-6, 2001, Rimini.

Porter, "Spinal Stenosis and Neurogenic Claudication," SPINE, Sep. 1, 1996, pp. 2046-2052, vol. 21, No. 17.

Pupin et al., "Clinical Experience with a Posterior Shock-Absorbing Implant in Lumbar Spine," World Spine 1: First Interdisciplinary World Congress on Spinal Surgery and Related Disciplines, Aug. 27-Sep. 1, 2000, Berlin, Germany.

Rengachary et al., "Cervical Spine Stabilization with Flexible, Multistrand Cable System," Techniques in Spinal Fusion and Stabilization, Hitchon et al., eds., 1995, pp. 79-81, Ch. 7, Thieme, New York.

Richards et al., "The Treatment Mechanism of an Interspinous Process Implant for Lumbar Neurogenic Intermittent Claudication," SPINE, 2005, pp. 744-749, vol. 30, No. 7.

Scarfò, "Instability/Stenosis: Holistic Approach for Less Invasive Surgery," date unknown, University of Siena, Siena, Italy.

Schiavone et al., "The Use of Disc Assistance Prosthesis (DIAM) in Degenerative Lumbar Pathology: Indications, Technique, Results," Italian J. Spinal Disorders, 2003, pp. 213-220, vol. 3, No. 2.

Schlegel et al., "The Role of Distraction in Improving the Space Available in the Lumbar Stenotic Canal and Foramen," Spine, 1994, pp. 2041-2047, vol. 19, No. 18.

Senegas et al., "Le Recalibrage du Canal Lombaire, Alternative à la Laminectomie dans le Traitement des Sténoses du Canal Lombaire," Revue de Chirurgie Orthopédique, 1988, pp. 15-22.

Senegas et al., "Stabilisation Lombaire Souple," Instabilité Vertébrales Lombaires, Gastambide, ed., 1995, pp. 122-132, Expansion Scientifique Française, Paris, France.

Senegas, "La Ligamentoplastie Inter Vertébrale Lombaire, Alternative a L'Arthrodèse," La Revue de Medécine Orthopédique, Jun. 1990, pp. 33-35, No. 20.

Senegas, "La Ligamentoplastie Intervertébrale, Alternative à L'arthrodèse dans le Traitement des Instabilités Dégénératives," Acta Othopaedica Belgica, 1991, pp. 221-226, vol. 57, Suppl. I.

Senegas, "Mechanical Supplementation by Non-Rigid Fixation in Degenerative Intervertebral Lumbar Segments: the Wallis System," Eur. Spine J., 2002, p. S164-S169, vol. 11, Suppl. 2.

Senegas, "Rencontre," Maîtrise Orthopédique, May 1995, pp. 1-3, No. 44.

Serhan, "Spinal Implants: Past, Present, and Future," 19th International IEEE/EMBS Conference, Oct. 30-Nov. 2, 1997, pp. 2636-2639, Chicago, Illinois.

Spadea et al., "Interspinous Fusion for the Treatment of Herniated Intervertebral Discs: Utilizing a Lumbar Spinous Process as a Bone Graft," Annals of Surgery, 1952, pp. 982-986, vol. 136, No. 6.

Sulzer Innotec, "DIAM—Modified CAD Geometry and Meshing," date unknown.

Taylor et al., "Analyse d'une expérience clinique d'un implant postérieur amortissant," Rachis Revue de Pathologie Vertébrale, Oct./Nov. 1999, vol. 11, No. 4-5, Gieda Inter Rachis.

Taylor et al., "Surgical Requirement for the Posterior Control of the Rotational Centers," date unknown.

Taylor et al., "Technical and Anatomical Considerations for the Placement of a Posterior Interspinous Stabilizer," 2004, pp. 1-10, Medtronic Sofamor Danek USA, Inc., Memphis, Tennessee.

Taylor, "Biomechanical Requirements for the Posterior Control of the Centers of Rotation," Swiss Spine Institute International Symposium: Progress in Spinal Fixation, Jun. 21-22, 2002, pp. 1-2, Swiss Spine Institute, Bern, Switzerland.

Taylor, "Non-Fusion Technologies of the Posterior Column: A New Posterior Shock Absorber," International Symposium on Intervertebral Disc Replacement and Non-Fusion-Technology, May 3-5, 2001, Spine Arthroplasty.

Taylor, "Posterior Dynamic Stabilization using the DIAM (Device for Intervertebral Assisted Motion)," date unknown, pp. 1-5.

Taylor, "Présentation à un an d'un dispositif amortissant d'assistance discale," 5èmes journées Avances & Controverses en pathologie rachidienne, Oct. 1-2, 1998, Faculté Libre de Médecine de Lille.

Tsuji et al., "Ceramic Interspinous Block (CISB) Assisted Anterior Interbody Fusion," J. Spinal Disorders, 1990, pp. 77-86, vol. 3, No. 1.

Vangilder, "Interspinous, Laminar, and Facet Posterior Cervical Bone Fusions," Techniques in Spinal Fusion and Stabilization, Hitchon et al., eds., 1995, pp. 135-146, Ch. 13, Thieme, New York.

Voydeville et al., "Experimental Lumbar Instability and Artificial Ligament," Eur. J. Orthop. Surg. Traumatol., Jul. 15, 2000, pp. 167-176, vol. 10.

Voydeville et al., "Lumbar Instability Treated by Intervertebral Ligamentoplasty with Smooth Wedges," Orthopédie Traumatologie, 1992, pp. 259-264, vol. 2, No. 4.

Waldemar Link, "Spinal Surgery: Instrumentation and Implants for Spinal Surgery," 1981, Link America Inc., New Jersey.

Wiltse et al., "The Treatment of Spinal Stenosis," Clinical Orthopaedics and Related Research, Urist, ed., Mar.-Apr. 1976, pp. 83-91, No. 115.

Wisneski et ai., "Decompressive Surgery for Lumbar Spinal Stenosis," Seminars in Spine Surgery, Wiesel, ed., Jun. 1994, pp. 116-123, vol. 6, No. 2.

Zdeblick et al., "Two-Point Fixation of the Lumbar Spine Differential Stability in Rotation," SPINE, 1991, pp. S298-S301, vol. 16, No. 6, Supplement.

Zucherman et al., "Clinical Efficacy of Spinal Instrumentation in Lumbar Degenerative Disc Disease," Spine, Jul. 1992, pp. 834-837, vol. 17, No. 7.

Anasetti et al., "Spine Stability After Implantation of an Interspinous Device: An In Vitro and Finite Element Biomechanical Study," J. Neurosurg. Spine, Nov. 2010, vol. 13, pp. 568-575.

Bellini et al., "Biomechanics of the Lumbar Spine After Dynamic Stabilization," J. Spinal Disord. Tech., 2006, vol. 00, No. 00, pp. 1-7.

Buric et al., "Diam Device For Low Back Pain In Degenerative Disc Disease 24 Months Follow up," Advances in Minimally Invasive Surgery And Therapy For Spine And Nerves, Alexandre et al., eds., 2011, pp. 177-182, Spinger-Verlat/Wien.

Phillips et al., "Biomechanics of Posterior Dynamic Stabilizing Device (DIAM) After Facetectomy and Discectomy," The Spine Journal, 2006, vol. 6, pp. 714-722.

Taylor at al., "Device For Intervertebral Assisted Motion: Technique and Initial Results," Neurosurg. Focus, Jan. 2007, vol. 22, No. 1, pp. 1-6.

Wilke et al., "Biomechanical Effect of Different Lumbar Interspinous Implants on Flexibility and Intradiscal Pressure," Eur. Spine J., vol. 17, published online Jun. 27, 2008, pp. 1049-1056.

Zhao et al., "Efficacy of the Dynamic Interspinous Assisted Motion System in Clinical Treatment of Degenerative Lumbar Disease," Chin. Med. J., 2010, vol. 123, No. 21, pp. 2974-2977.

* cited by examiner

APPARATUS FOR INSERTION BETWEEN ANATOMICAL STRUCTURES AND A PROCEDURE UTILIZING SAME

BACKGROUND

The present invention relates to an apparatus for insertion between anatomical structures and a procedure utilizing same and, more particularly, to such an apparatus that includes a member that is compressed before it is inserted and expands after it is inserted.

It is often desirable to insert a device between anatomical structures for several reasons. For example, it can be inserted in a manner so that it engages the structures and serves as an implant for stabilizing the structures and absorbing shock. Alternately, a device can be temporarily inserted between the structures and function to distract the structures to permit another device, such as a prosthesis, to be implanted between the structures. According to another example, a device can be inserted between the structures to distract the structures to permit another surgical procedure to be performed in the space formed by the distraction, after which the device is released and removed.

Although devices have been designed for one or more of the above uses they are not without problems. For example, it is often difficult to insert the device without requiring excessive invasion of the anatomy, damage to the adjacent anatomical structures, or over-distraction. Embodiments of the present invention improve upon these techniques and various embodiments of the invention may possess one or more of the above features and advantages, or provide one or more solutions to the above problems existing in the prior art.

DETAILED DESCRIPTION

Figure 1:
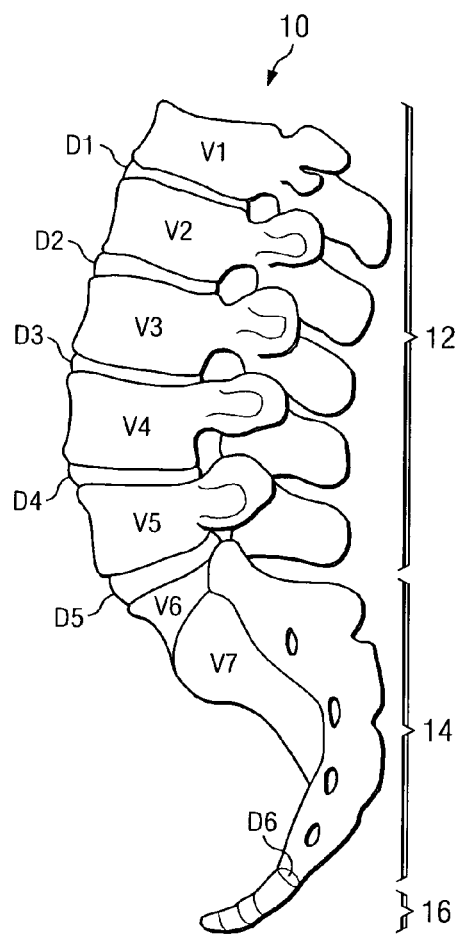
FIG. 1 is a side elevational view of an adult human vertebral column.
Figure 2:
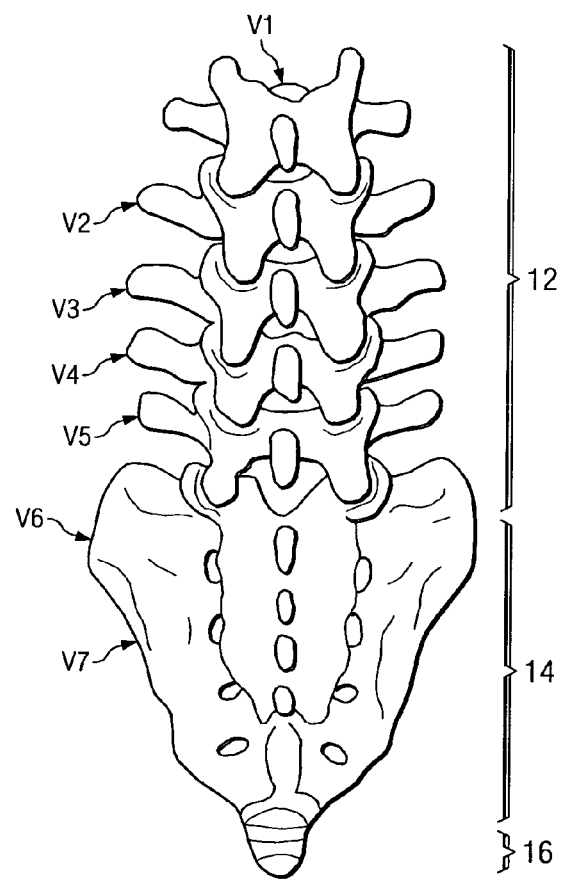
FIG. 2 is a posterior elevational view of the column of FIG. 1.

With reference to FIGS. 1 and 2, the reference numeral 10 refers, in general, to the lower portion of a human vertebral column 10. The column 10 includes a lumbar region 12, a sacrum 14, and a coccyx 16. The flexible, soft portion of the vertebral column 10, which includes the thoracic region and the cervical region, is not shown.

The lumbar region 12 includes five vertebrae V1, V2, V3, V4 and V5 separated by intervertebral discs D1, D2, D3, and D4, with the disc D1 extending between the vertebrae V1 and V2, the disc D2 extending between the vertebrae V2 and V3, the disc D3 extending between the vertebrae V3 and V4, and the disc D4 extending between the vertebrae V4 and V5.

The sacrum 14 includes five fused vertebrae, one of which is a superior vertebrae V6 separated from the vertebrae V5 by a disc D5. The other four fused vertebrae of the sacrum 14 are referred to collectively as V7. A disc D6 separates the sacrum 14 from the coccyx 16, which includes four fused vertebrae (not referenced).

Figure 3:
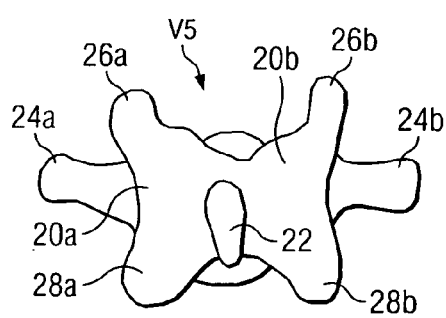
FIG. 3 is an elevational view of one of the vertebrae of the column of FIGS. 1 and 2.

With reference to FIG. 3, the vertebrae V5 includes two laminae 20a and 20b extending to either side (as viewed in FIG. 2) of a spinous process 22 that extends posteriorly from the juncture of the two laminae. Two transverse processes 24a and 24b extend laterally from the laminae 20a and 20b, respectively; two articular processes 26a and 26b extend superiorly from the laminae 20a and 20b respectively; and two articular processes 28a and 28b extend inferiorly from the laminae 20a and 20b, respectively. The inferior articular processes 28a and 28b rest in the superior articular process of the vertebra V2 to form a facet joint. Since the vertebrae V1-V4 are similar to the vertebrae V5, and since the vertebrae V6 and V7 are not involved in the present invention, they will not be described in detail.

Figure 4A:
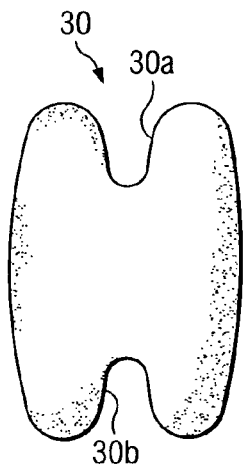
FIG. 4A-4C are elevational views depicting apparatus for inserting in the column of FIGS. 1-3.
Figure 4B:
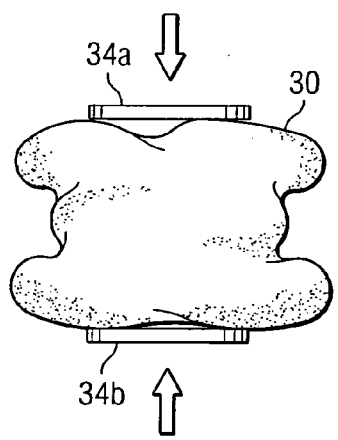
Figure 4C:
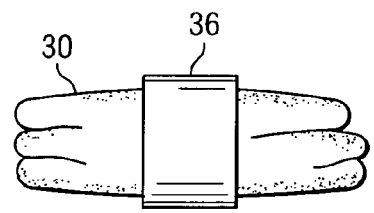

It will be assumed that, for one or more of the reasons set forth above, the vertebrae V3 and V4 are not being adequately supported by the disc D4, and that it is therefore necessary to provide supplemental support and stabilization of these vertebrae. To this end, and referring to FIGS. 4A-4C, a device 30 according to an embodiment of the invention is implanted between the respective spinous processes 22 of the vertebrae V3 and V4.

The device 30 is generally rectangular in shape with two notches, or saddles, 30a and 30b formed at each end. The device 30 is fabricated from a soft flexible material that has a predetermined shape and elastic properties that will permit it to return towards its original state after it has been compressed. Examples of this type of material are polyurethane, rubber, RTV silicone, two-part silicone, silicone, two-part urethane PA, hydrogels, collagen matrix, bone matrix, ceramic granules suspended in an aqueous fluid, morsalized fascia, silk elastin, polymer proteins, proteins, protein hydrogel, and thermopolymer. Also, the device can be fabricated from a fabric and dipped in silicone thereby providing a memory, or preset shape, of the device to guide it during expansion.

Before the device 30 is implanted it undergoes a series of steps. Initially a compressive force, or load, is applied to the side walls of the device in a direction perpendicular to the axis of the device as shown by the arrows in FIG. 4B. This load can be applied by any mechanical device such as a vice, or the like, having two plates 34a and 34b that engage the respective side walls of the device 30. Equal and opposite forces are applied to the plates 34a and 34b in one plane in the directions of the arrows in any known manner, and the amount of the forces are regulated so that the device is compressed to a shape generally shown in FIG. 4C.

The plates 34a and 34b are released and a retaining ring 36 is immediately placed over the compressed device at a location approximately between its ends. The ring 36 thus prevents the device 30 from returning back to its original shape shown in FIG. 4A.

Figure 5A:
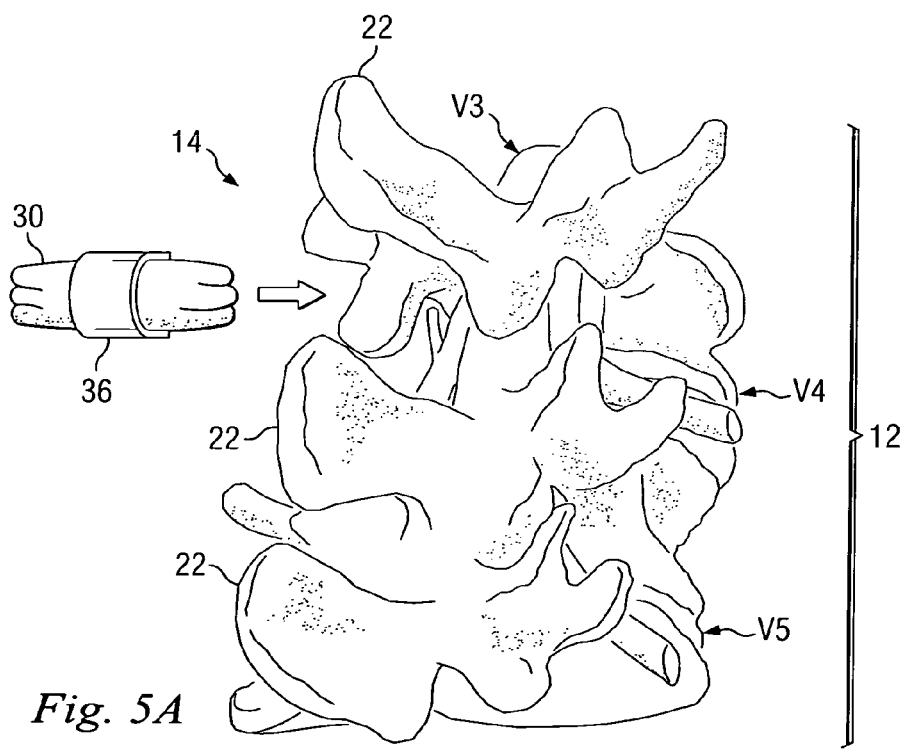
FIG. 5A-5C are enlarged, partial, isometric views of a portion of the column of FIGS. 1 and 2, including the lower three vertebrae of the column, and depicting a procedure for inserting the apparatus of FIGS. 4A-4C between two adjacent vertebrae.
Figure 5B:
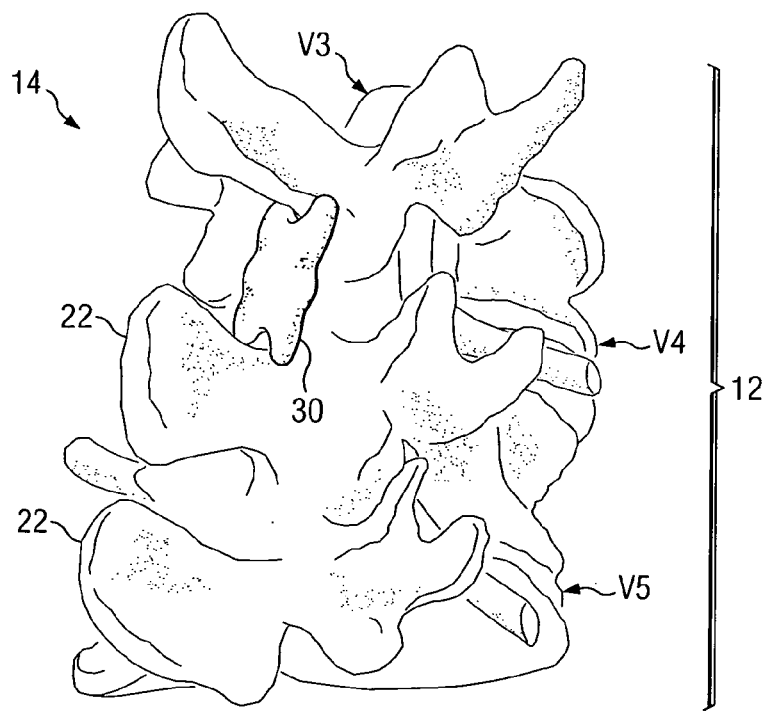
Figure 5C:
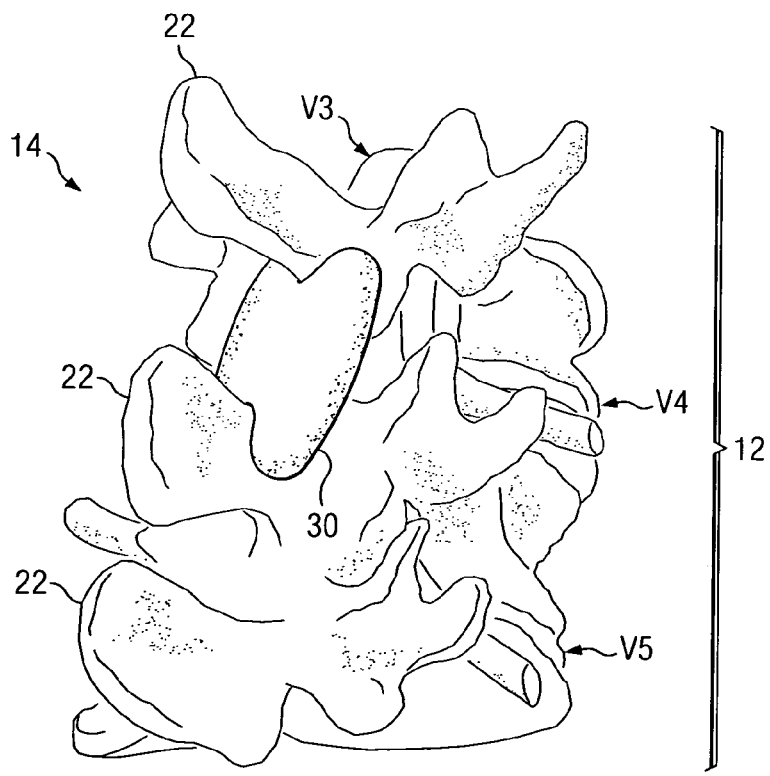

The apparatus consisting of the device 30, in its compressed shape, and the retaining ring 36 extending around the device, is inserted between the respective spinous processes 22 of the vertebrae V3 and V4 in the direction shown in FIG. 5A. Then the ring 36 is removed from the compressed device 30 and the memory characteristic of the material of the device, as discussed above, causes the device to start expanding in a manner towards its original shape. FIG. 5B depicts an intermediate stage of the expansion of the device 30 as it expands from the fully compressed position of FIG. 5A to its fully expanded position as shown in FIG. 5C. In the last position, the device 30 engages the spinous processes 22 of the vertebrae V3 and V4, respectively, with enough force to firmly secure the device between the processes and stabilize the vertebrae. It is understood that, in moving from the position of FIGS. 5B to 5C, the device 30 can engage and move at least one of the processes 22 slightly if it is desired to establish a predetermined spatial relationship between the processes.

In addition to stabilizing the vertebrae V3 and V4, the relatively flexible, soft material of the device 30 readily conforms to the processes and provides excellent shock absorption and deformability, resulting in an improved fit.

Figure 6A:
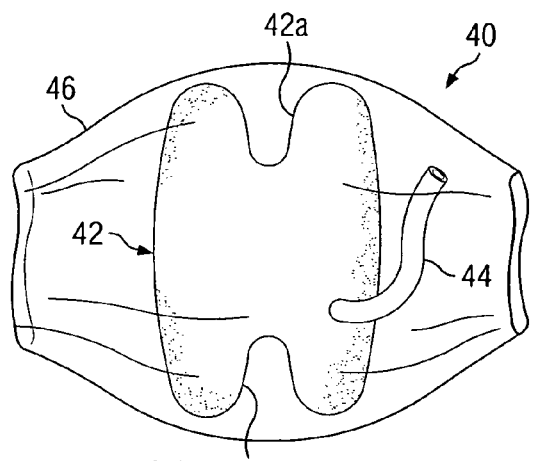
FIG. 6A-6D are elevational views depicting apparatus according to an alternate embodiment for inserting in the column of FIGS. 1-3.
Figure 6B:
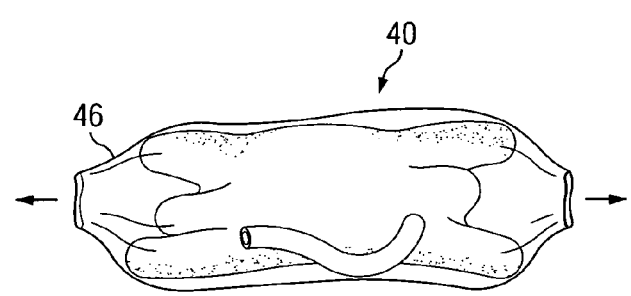
Figure 6C:
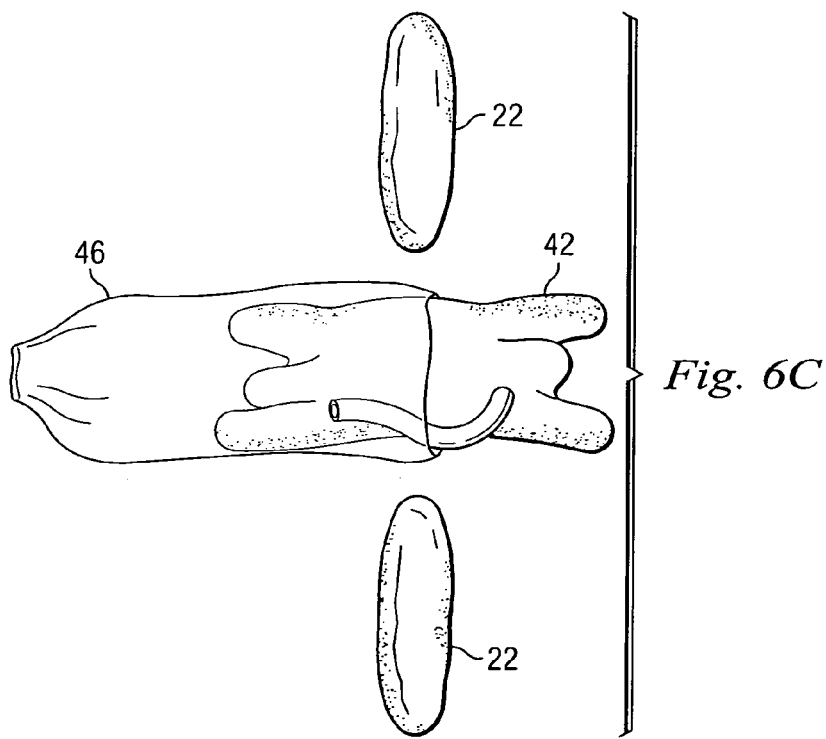

Referring to FIGS. 6A-6C, the reference numeral 40 refers to, in general, an implantable device according to another embodiment of the present invention. As in the previous embodiment, the device can be implanted between two spinous processes, such as the processes 22 associated with the vertebrae V3 and V4 as depicted in FIGS. 5A-5C.

The device 40 comprises a hollow body member 42, generally rectangular in shape, and having two notches, or saddles, 42*a* and 42*b*, formed at each end. The body member 42 is fabricated from a soft flexible material that will deform, or compress, under load conditions to be described.

One end of a tube 44 registers with an opening in the body member 42, and the other end of the tube is adapted to be connected to a source of fluid (not shown) so that the fluid can be introduced into the interior of the body member. Examples of the type of fluid that can be used are air, water, and a curable polymer. The quantity of fluid introduced into the interior of the body member 42 is controlled so that the body member will expand in a manner to be described.

A sack, or sheath, 46 extends over the body member 42 and is sized so as to fit relatively tight in the axial direction, that is, the width of the sheath is only slightly greater that the length of the body member. The sheath 46 has two open ends so that the body member 42 can be inserted into and removed from, the sheath through either end. Preferably the sheath 46 is fabricated from a type of material that is heat shrinkable, that is, it will shrink when subjected to sufficient heat. Since this type of material is conventional it will not be described in detail.

Figure 7A:
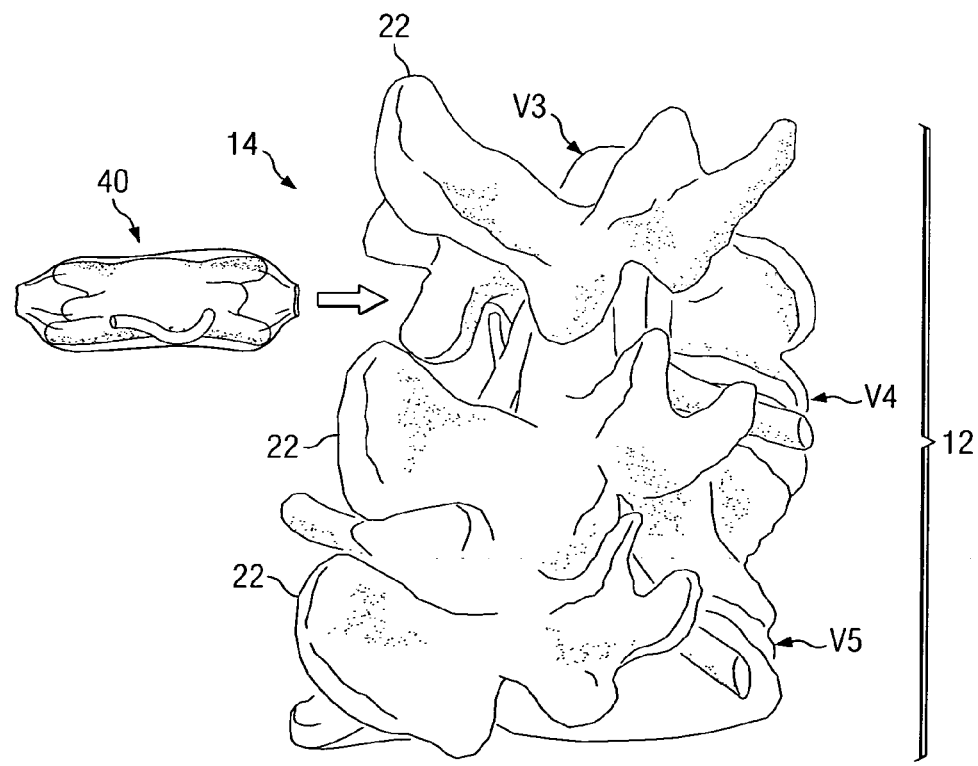
FIG. 7A-7C are enlarged, partial, isometric views of a portion of the column of FIGS. 1 and 2, including the lower three vertebrae of the column, and depicting a procedure for inserting the apparatus of FIGS. 6A-6D between two adjacent vertebrae.

After the body member 42 is inserted in the sheath 46, heat is applied to the sheath in any conventional manner. As a result, the sheath 46 shrinks to the position shown in FIG. 6B and compresses the body member 42 in a manner that considerably reduces its axial length. The device 40 is then inserted between the respective spinous processes 22 of the vertebrae V3 and V4 in the direction shown in FIG. 7A, while the sheath retains the body member 42 in its compressed state.

Figure 6D:
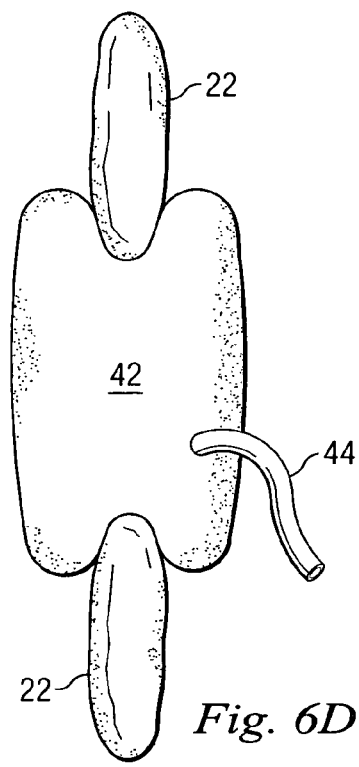
Figure 7B:
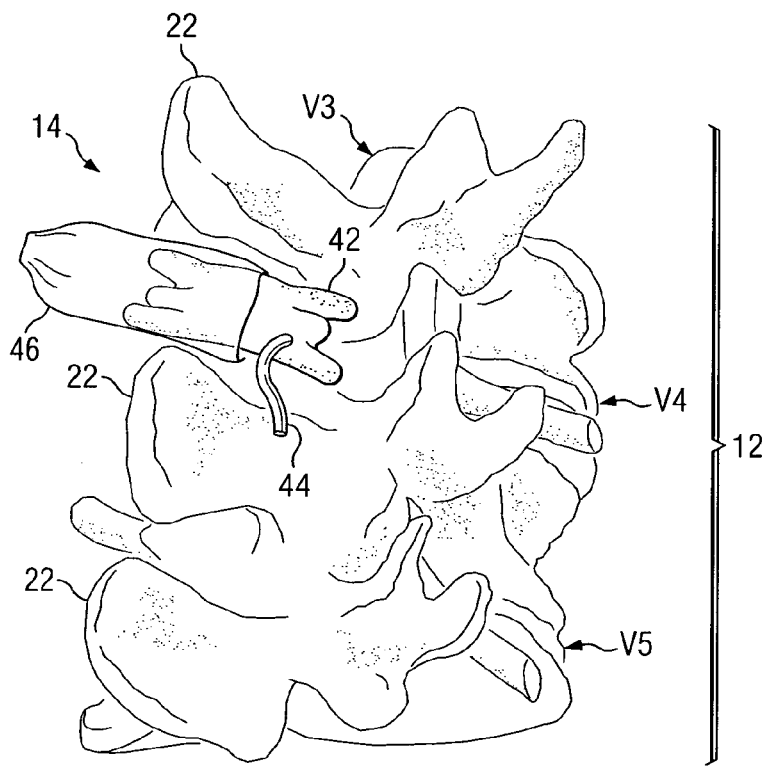
Figure 7C:
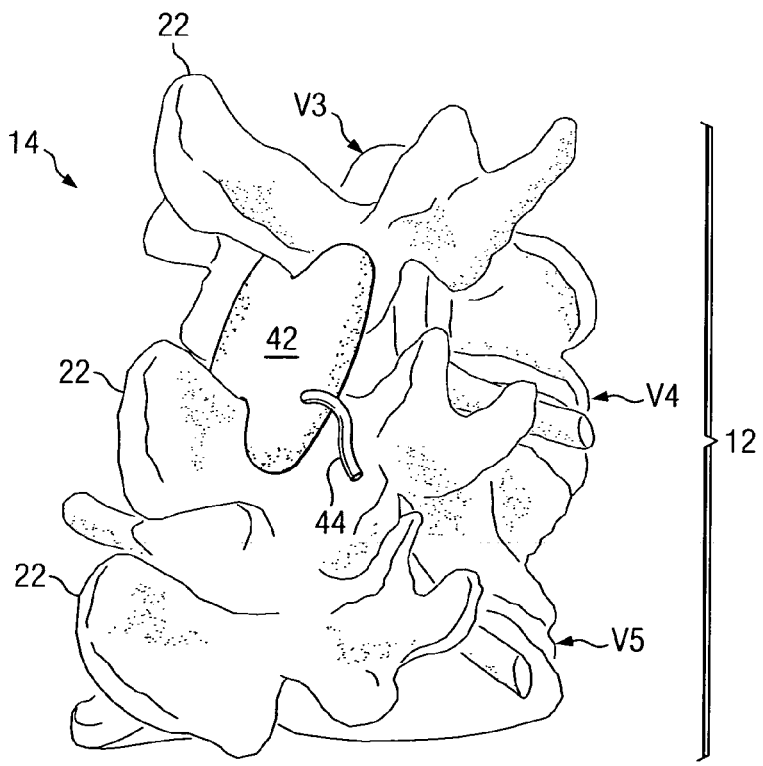

The sheath 46 is then removed from the body member 42 by pulling on one end of the sheath, as shown in FIGS. 6C and 7B. Fluid is then introduced into body member 42, via the tube 44, and the body member starts expanding until it reaches its fully expanded position as shown in FIGS. 6D and 7C. The fluid flow is terminated when the body member 42 engages the respective spinous processes 22 of the vertebrae V3 and V4 with enough force to stabilize the vertebrae. It is understood that, in moving from the position of FIG. 7B to FIG. 7C, the body member 42 can engage and move at least one of the processes 22 slightly if it is desired to establish a predetermined spatial relationship between the processes.

The device 40 is thus firmly secured in its implanted position shown in FIG. 7C. In addition to stabilizing the vertebrae V3 and V4, the relatively flexible, soft material of the body member 42 readily conforms to the respective processes 22 of the vertebrae and provides excellent shock absorption and deformability, resulting in an improved fit.

According to an alternate version of the embodiment of FIGS. 6A-6C, the sheath 46 can be scored or perforated so that it does not have to be manually removed from the body member 42 after insertion between the spinous processes 22. Rather, the sheath 46 can be left on the body member 42 after the insertion of the device between the process 22. The scores or perforations will cause the sheath 46 to break apart during the introduction of the fluid into the interior of the body member 42 and allow the body member to expand into engagement with the processes 22 as described above.

In each of the foregoing embodiments, it is understood that the term "expand", as used above is meant to cover the situation in which the body member 42 is allowed to move back towards its normal state when the sheath is removed after it was initially contracted when put in the sheath 46; or the situation in which the body member is actually inflated in response to the introduction of the fluid; or both.

It is also understood that, in each of the above embodiments the devices 30 and 40 do not necessarily have to function as implants between two processes as described in the examples above, but rather can be used in other different procedures and in other different areas of the anatomy. For example, the devices 30 and 40 can be inserted between the two anatomical structures, such as the processes used in the above examples, and expanded to an extent that it engages and distracts, or moves, the structures in a direction away from each other, to permit another device, such as a prosthesis, to be implanted between the structures or in an area near the structures. According to another example, each device can be inserted between the structures and expanded to an extent that it engages and distracts the structures to permit another surgical procedure to be performed in the space formed by the distraction. In each of these examples, the device would be released and removed after the procedure is completed.

Variations

It is understood that variations may be made in the foregoing without departing from the invention and examples of some variations are as follows:

(1) The device 30 and the body member 42 can take shapes that are different from the examples disclosed above.

(2) The devices 30 and 40 can be inserted in other areas of the anatomy such as, for example, in an intervertebral disc space represented by the references D1-D5 in FIG. 1 or between the transverse processes 24*a* and 24*b*.

(3) The devices 30 and 40 can be inserted between two vertebrae following a corpectomy in which at least one vertebrae is removed.

(4) The members used to retain the device 30 and the body member 42 in their compressed condition can vary.

(5) The types of fluid introduced into the body member 42 can be vary.

(6) The expansion of the device 30 and the body member 42 can be such that they engage only one of the anatomical structures.

(7) In the embodiment of FIGS. 6A-6C, the body member 42 can be compressed in the sheath 46 by techniques other than heat shrinking the sheath, such as, for example, stretching the sheath so that it changes from the shape shown in FIG. 6A to the shape shown in FIG. 6B.

(8) Any spatial references made above, such as "under", "over", "between", "upper", "lower", "top", "bottom", etc. are for the purpose of illustration only and do not limit the specific orientation or location of the structure described above.

The preceding specific embodiments are illustrative of the practice of the invention. It is to be understood, therefore, that other expedients known to those skilled in the art or disclosed herein, may be employed without departing from the invention or the scope of the appended claims, as detailed above. In the claims, means-plus-function clauses are intended to cover the structures described herein as performing the recited function and not only structural equivalents but also equivalent structures. Thus, although a nail and a screw may not be structural equivalents in that a nail employs a cylindrical surface to secure wooden parts together, whereas a screw employs a helical surface, in the environment of fastening wooden parts, a nail and a screw are equivalent structures.

What is claimed is:

1. A surgical apparatus comprising:
   an expandable member having a pair of upper arms extending upwardly from a central body and forming an upper saddle and a pair of lower of arms extending downwardly from the central body and forming a lower saddle;
   the upper saddle having a minimum point therealong disposed closest to a center of the member and the lower saddle having a maximum point therealong disposed closest to the center of the member;
   a sheath adapted to contain the member and adapted to be heated to compress the member such that the minimum and maximum points of the upper and lower saddles respectively move toward each other and each of the upper and lower arms extend in a generally lateral direction from the central body so that the member can be inserted between two adjacent spinous processes;
   wherein when the member is compressed one of the upper arms and one of the lower arms extend in a first direction and the other of the upper arms and the other of the lower arms extend in a second direction, generally opposite from the first direction;
   a conduit for introducing fluid into the member to expand the member into engagement with at least one of the spinous processes.

2. A surgical procedure comprising:
   inserting a member into a sheath, the member having a pair of upper arms extending upwardly from a central body and forming an upper saddle and a pair of lower arms extending downwardly from the central body and forming a lower saddle; the upper saddle having a minimum point therealong disposed closest to a center of the member and the lower saddle having a maximum point therealong disposed closest to the center of the member;
   heating the sheath to cause shrinkage of the sheath and compression of the member such that:
      the minimum and maximum points of the upper and lower saddles respectively move toward each other;
      one of the upper arms and one of the lower arms extend in a first direction;
      the other of the upper arms and the other of the lower arms extend in a second direction, generally opposite from the first direction;
   inserting the sheath containing the compressed member between two adjacent spinous processes;
   introducing fluid into the member to expand the member;
   terminating the step of introducing when the member is in engagement with at least one of the spinous processes.

3. The procedure of claim 2 wherein the sheath is manually removed from the member prior to the step of introducing.

4. The procedure of claim 2 wherein the fluid is selected from a group consisting of air, water, and a curable polymer.

5. The procedure of claim 2 wherein the expansion of the member causes distraction between the spinous processes.

* * * * *